March 10, 1953 C. W. FISCHER Plant Pat. 1,173

SAINTPAULIA PLANT

Filed Oct. 2, 1947 2 SHEETS—SHEET 1

Inventor:

Charles W. Fischer,

By Cushman, Darby & Cushman

Attorneys.

Inventor:
Charles W. Fischer,
By Cushman, Darby & Cushman
Attorneys.

Patented Mar. 10, 1953

Plant Pat. 1,173

UNITED STATES PATENT OFFICE 1,173

SAINTPAULIA PLANT

Charles W. Fischer, Atlantic City, N. J.

Application October 2, 1947, Serial No. 777,568

1 Claim. (Cl. 47—60)

The present invention relates to a new and distinct variety of Saintpaulia plant, commonly known as the African violet, the new variety having the dominant characteristic of a plurality of rows or layers of petals, as distinguished from the single row of petals as is present in the flower of the common African violet plant.

The plant of the present invention was initially asexually reproduced from a mutation flower which exhibited the distinct characteristics referred to, said mutation appearing on a Saintpaulia plant known as the "Blue Boy" variety, in a greenhouse of my nursery at Linwood, New Jersey.

The new and distinct variety of plant claimed herein is identical with the well known variety, Blue Boy (unpatented), except as specifically noted herein. Like the Blue Boy, the growth is vigorous and the flowering profuse. The leaves of my new variety have the general characteristics of leaves of the Blue Boy. They are thick, soft, broad, and covered with a fine hairy fuzz over the surface, and are olive, dusky green in color on their top surface (41 Plate—"Ridgeway's Color Standards and Nomenclature"). The undersurfaces of the leaves are pale green, with a distinctive heavy vein ascending toward the apex. The leaves range in size approximately from 1¼ inch by 1 and ¾ inch to 2 and ¾ inch by 3¼ inch. The leaf stems are of medium length and are from ⅛ inch to $\frac{3}{16}$ inch in diameter.

The flower of the new variety is about one inch in diameter and is pompon in shape with about fourteen petals to the flower as an average, and these petals are circularly arranged one above another to form a plurality of layers of petals, as distinguished from the single petal arrangement of the Blue Boy variety. While the average number of petals per flower is fourteen, as many as seventeen petals per flower have been noted. The new variety has proved itself to be a continuous bloomer under cultivation, and the individual blooms endure several weeks after opening.

The new and distinct variety was first discovered by me at a time when I had under cultivation and observation, Saintpaulia plants of the Blue Boy variety, which variety I had under cultivation for improvement by the selection of the superior plants for reproduction. The new variety appeared as a mutation on one part of one of the Blue Boy plants then under cultivation and improvement in my greenhouses at Linwood, New Jersey. Having discovered and noted the distinct characteristics of the mutation, I observed it from time to time and thereafter reproduced from this plant asexually by leaf cuttings, numerous plants, several thousand of which have now reached flowering size and have retained the distinctive characteristics referred to herein. These new plants so reproduced asexually, had flowers which retained the color of the original sport, i. e., that of the Blue Boy variety.

In addition to the dominant characteristic referred to, the new variety of the present application has the following other features which distinguish it from its parent, the Saintpaulia of the Blue Boy variety, which appear in plants as reproduced by leaf cuttings; (*a*) each flower stem carries more individual flowers than are carried by the common varieties, (*b*) only a few of the flowers produce pollen sacs, and (*c*) old flowers do not drop off the stem but simply dry up, and must be picked off. The last-mentioned feature makes the new variety quite superior to common varieties as a house plant.

The color of the petals of the original sport, and asexual reproductions therefrom, may be best described as blue purple (No. 76, Smico standard) from the "Smico Color Selector."

Most of the flowers lack the double yellow pollen sacs characteristic of the single varieties. When these pollen sacs appear, they are not always in the center of the flower.

Other than the above, the new and distinct variety of plant claimed herein has all of the characteristics of the common and well known varieties of Saintpaulia, including growth habits. The new variety is distinguished by its entirely different flower type, the individual blossoms being multi-petaled or double, rather than possessing only a single row of flower petals as in the case of all common types of African violets in existence. The new variety distinguishes from common varieties of the African violet in that the flower stems rising from the base of the plants, carry many more individual blooms, and these double blooms do not drop their petals quickly like the more conventional varieties.

In the drawings, which are photolithographic reproductions of a plant of the new variety.

Figure 1:
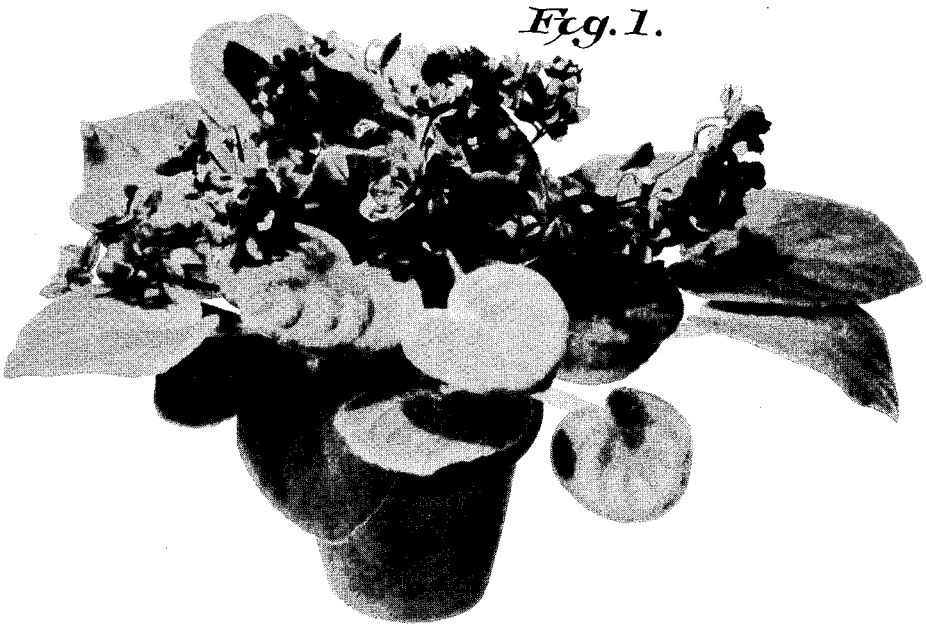
Figure 1 is a side view of a potted plant of the new variety.
Figure 2:
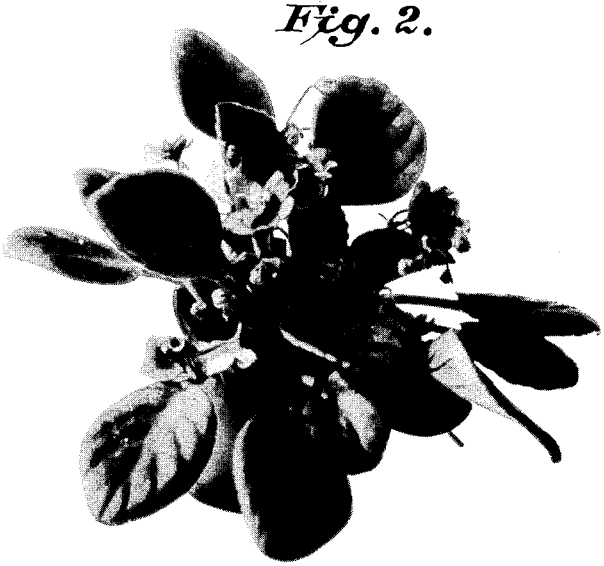
Figure 2 is a view of a potted plant looking generally downwardly thereon.
Figure 3:
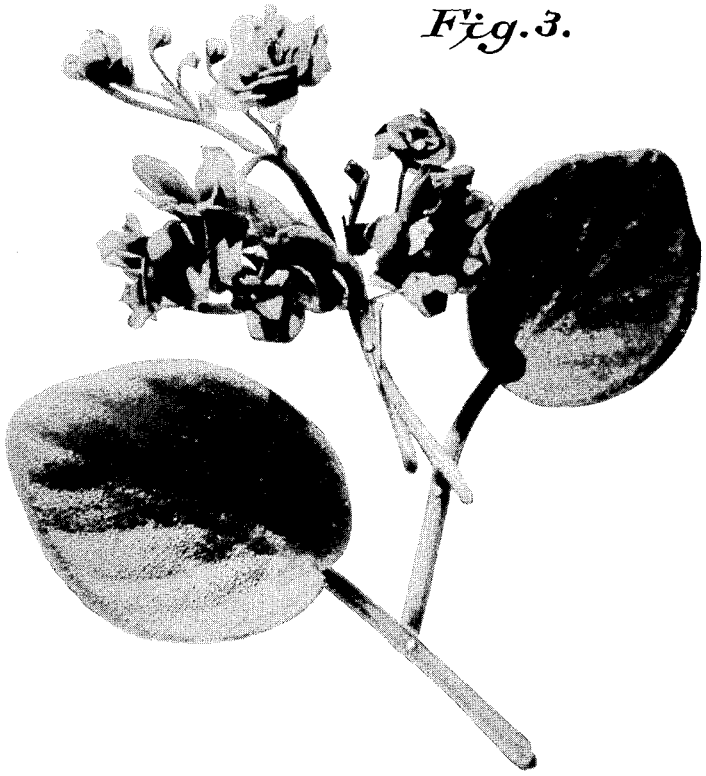
Figure 3 is an enlarged view of the leaves and a flower stem.
Figure 4:
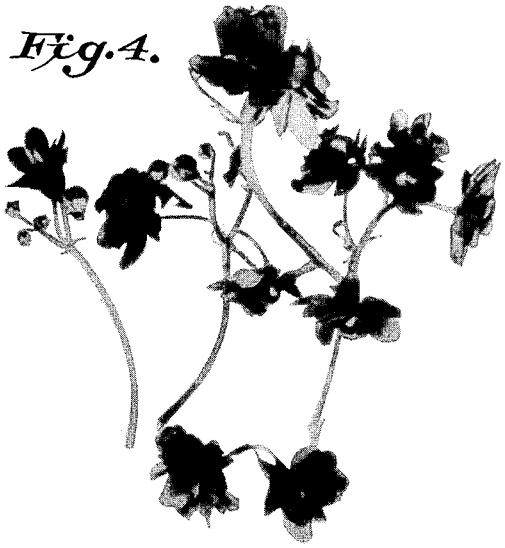
Figure 4 is an enlarged view of a number of the flowers, showing the multiple petal characteristic.

Having described my invention or discovery as completely as it is reasonably possible for me to do, I claim:

A new and distinct variety of Saintpaulia plant substantially as herein disclosed, characterized by flowers having a plurality of rows or layers of petals.

CHARLES W. FISCHER.

REFERENCES CITED

The following references are of record in the file of this patent:

Jackson, "Glossary of Botanic Terms," 4th ed., 1928, pp. 118 and 151.

Garden Dictionary, published 1938, page 153.

Garden Encyclopedia, published 1939, pages 279 and 387.

Bailey, "Standard Cyclopedia of Horticulture," published 1943, vol. 2, page 1249.

Wilson, "African Violets as a Hobby," published November 28, 1945, by Curtis Publ. Co., Phila., copyright No. AA-499, 954, pages 3, 4, 8, 9, and two unnumbered pages preceding page 3.

Tinari Flower Gardens, Fall List—1946, published Sept. 1946; two pages.

Spoutz, "African Violets, Spring 1948 Catalog," published Jan. 25, 1948, copyright No. KK-20,924, cover and pages 5 and 9.

Spoutz, "African Violets, Fall 1948 Catalog," published 1948, cover and pages 6 and 9.

"The African Violet," by Helen Van Pelt Wilson, first edition (1948), pages 73, 116, 120, 121, 134, 174, 176.

Wilson "The African Violet," 5th ed., published March 1949, pp. 134, 135, 136, 178.